US005376042A

United States Patent [19]

Reber et al.

[11] Patent Number: 5,376,042

[45] Date of Patent: Dec. 27, 1994

[54] PROCESS FOR THE DEPILATION OF ANIMAL SKINS

[75] Inventors: Raymond E. Reber; Alcides B. da Silva; Joao B. Tognetti, all of Sao Paulo, Brazil

[73] Assignee: Peroxidos do Brasil Ltd., Sao Paulo, Brazil

[21] Appl. No.: 901,608

[22] Filed: Jun. 19, 1992

[30] Foreign Application Priority Data

Jun. 19, 1991 [BR] Brazil .............................. PI 9102563

[51] Int. Cl.$^5$ .......................... C14C 1/06; A61K 7/00; A22B 5/08

[52] U.S. Cl. ...................................... 452/71; 8/94.16; 424/45

[58] Field of Search ............... 452/71, 81, 45; 424/45, 424/47, 71, 74, 94.6, 195.1, 175, 78.38; 8/94.16, 94.15, 94.17, 94.18

[56] References Cited

U.S. PATENT DOCUMENTS

| | | | |
|---|---|---|---|
| 2,225,601 | 12/1940 | Pfannmuller | 8/94.16 |
| 3,628,910 | 12/1971 | Grayson | 8/94.16 |
| 4,122,159 | 10/1978 | Madrange | 424/45 |
| 4,548,608 | 10/1985 | Swanson et al. | 8/94.16 |
| 4,636,222 | 1/1987 | Pfleiderer et al. | 8/94.16 |
| 5,149,295 | 9/1992 | Bowling et al. | 452/71 |

FOREIGN PATENT DOCUMENTS

| | | |
|---|---|---|
| 160036 | 6/1964 | Brazil . |
| 8304115 | 8/1983 | Brazil . |
| 1145359 | 3/1967 | United Kingdom . |
| 1106391 | 3/1968 | United Kingdom . |
| 1114068 | 5/1968 | United Kingdom . |
| 1469725 | 4/1977 | United Kingdom . |
| 931744 | 5/1982 | U.S.S.R. . |
| WO90/01023 | 2/1990 | WIPO . |

OTHER PUBLICATIONS

Christner, J. "The Pros and Cons of a Hair-Savie Process In The Beamhouse:", Fonte: The Journal of the American Leather Association, vol. 83, pp. 183-192, 1988.

Abstract in English of German Patent Application No. 808,740.

Abstract of Japanese Application 69/21385.

Translation into Portuguese of Japanese application 54-10601.

*Primary Examiner*—Willis Little

*Attorney, Agent, or Firm*—Larson and Taylor

[57] ABSTRACT

Current enzymatic processes for the depilation of hair require long processing times and are relatively expensive and chemical processes often create odor and/or effluent disposal problems. In the present invention, skins to be depilated are contacted with an oxidizing solution in the form of foam, instead of the liquid compositions previously used. The foam normally comprises an oxidizing agent, a pH regulator and a surfactant composition with a high foaming power. The oxidizing agent is preferably hydrogen peroxide or peracetic acid. After the oxidation of the hair, the foam is preferably caused to collapse and depilation is desirably completed in a mechanical stage. In this process, the amount of fluid coming into contact with the skins during the depilation stage is minimized, thus reducing intumescence and, secondly, the amount of effluent.

24 Claims, No Drawings

PROCESS FOR THE DEPILATION OF ANIMAL SKINS

The present invention relates to the technical field of processes aimed at the preparation of animal skins for subsequent tanning and finishing, and in particular to processes for the depilation of the skins.

The aim of animal skin processing treatments is usually to produce a stable and imputrecible material (leather) widely used for making articles for industrial use and clothing. Skins are often salt-containing and stored for long periods before they are processed. The process for the preparation of the material normally includes the removal of salt from and the hydration of skins which had previously been salted, by a soaking stage, sometimes called a steepage process, followed by the removal of hair.

Apart from replacing water which was removed during storage, the steepage process also seeks to clean the skins by eliminating impurities adhering to the hair and to extract soluble proteins and interfibrillar materials. The effects of factors which influence the efficacy of steepage such as the quality of the water, the temperature, the time, the agitation of the bath, the type of storage, the grading of the skins, the use of auxiliary agents and the bath ratio are widely known and allowance can be made for them.

Processes for the removal of hair and the epidermal system have already been the subject matter of publications using enzymatic, chemical/enzymatic or chemical processes.

The enzymatic processes are usually carried out by hydrolysis of specific proteins, glyco-proteins and proteoglycanes in the basal membrane. This hydrolysis is carried out with specific fungic or bacterial proteases which generally can provide satisfactory results with respect to the removal of hair. The principle disadvantage of this type of process is the need for a subsequent extra treatment in order to obtain the necessary softening effect on the fibre structure for a better effectiveness of the tanning agents. Other disadvantages that have also been mentioned in descriptions of the state of the art are the unsatisfactory quality of the leather obtained sometimes, due to damage of the hair side of the hide, the high cost and the long processing times. These negative aspects have been confirmed by W. Fendrup in an article published in Leather Technology Chemistry 58, 9 (1974) in which, as an example of conventional enzymatic depilation, a steepage treatment is described at pH 9 to 10 with specific fungic and bacterial protease which has a process time of not less than 18 to 24 hours.

The use of combined chemical/enzymatic processes is also well known. German Patent Application 888.740 filed by Rohm and Haas GmbH on 8 Feb. 1936 discloses the use of hydrogen peroxide and nitrates as activators for enzymatic depilation baths. Another Japanese application, No. 69/21385, filed by Y. EBARA on 6 Jun. 1962 discloses the removal of hair from the skins of edible animals by using proteolytic enzymes, hydrosulphites and lime prior to steepage in a solution of hydrogen peroxide for deodorisation and bleaching. A similar course of action is taken in French application No. 74/026.342, filed by Omnium Prospective Industrielle on 30 Jul. 1974 which describes the recovery of hair from skins steeped by treatment at a pH above 8 in baths containing sodium perborate, urea and sodium chloride followed by the addition of bacterial protease, the bath temperature being of the order of 50° C. In the first and second case, the objective is the removal of the hair with recovery of the skin. The disadvantages of such a combined process continue to be those mentioned above for enzymatic process, mainly the high cost and the long processing times. In the third reference, the objective is the recovery of the hair from the skins, which is dissolved by enzymatic action and temperature. However, this does not apply in the case described in the present invention.

The use of chemical processes for the removal of hair and the epidermal system is undoubtedly the most widespread, comprising the largest number of articles published. Traditionally, chemical agents used are those which act directly on the keratin causing a breakdown of the disulphide cross-links of the amino acid molecules, mainly cystine. The resistance of the hair decreases when these cystine disulphide cross-links are broken, finally causing the disintegration of the keratin structure. The chemical agents used at present for tanning are sodium sulphide and calcium hydroxide. The main advantage of such processes is the low cost of dehairing the skins. The disadvantages usually mentioned are the need to subsequently remove the lime in a separate process, the unpleasant odours caused by the release of hydrogen sulphide gas and mainly, the formation of highly noxious effluent requiring cumbersome treatment before it becomes suitable for discharge into water courses without damaging the environment.

In order to improve the well-known disadvantages of this process, investigations have been carried out using:

(a) treatment or recycling operations of the effluent formed or (b) lower sulphide contents in depilation or (c) other chemical agents completely replacing the sulphide.

In this connection, the main advances have occurred in the area of the total replacement of the sulphides since, apart from the process problems mentioned above, the pressures exerted by society and the national and international organisations are increasing considerably against the pollution of the environment caused by the discharge of effluents and especially of sulphides. It is estimated that in the case of the present technologies using sodium sulphide, 80% of the biological oxygen demand of the effluents caused by the preparation of chrome-tanned leathers are due to the depilation baths.

Various patent references recommending this total replacement of sulphides by other chemical agents are known. British patent no. 1145359 dated 31 Mar. 1966 and Brazilian patent no. 160036 dated 26 Jun. 1964 use chlorine dioxide formed in an acid medium from chlorites. These are processes which make it possible to obtain skins with a firm, clean hair side with a low intumescence. However, its slow action on the keratin tends to impair the quality of the leather. In addition, these processes have other serious drawbacks including, for example, corrosion and the high toxicity of the chlorine and chlorine dioxide as well as their damaging effect on the collagen which reduces the resistance to stress of the leather. Another serious disadvantage is the handling of sodium chlorite both in the solid form and in concentrated solution which can cause explosions and fire in the case of carelessness.

Other possibilities for replacing sulphide, including the use of peroxides, have also been mentioned in the prior art. Cases of these are the British Patent Nos. 1106391 and 1114068 filed by Deutsche Gold und Silberscheideanstalt vormals Roessler, Degussa, making use of organic and inorganic peracids and the salts thereof (e.g. peracetic acid, permonosulphuric acid and also inorganic peroxides). These are efficient processes as regards the removal of hair and moreover provide the possibility of additional bleaching of the skins. However, the high cost of peracids, particularly of peracetic acid and permonosulphuric acid for this application and in particular the high corrosiveness of these products make their use impracticable on a large scale.

In the specific case of hydrogen peroxide, German patent no. D-46904 filed by Degussa on 26 Mar. 1965 describes a composition suitable for the depilation of skins, consisting of a solution of this peroxide in the presence of an amine in an alkaline medium. In addition, Japanese patent application No. 54-10601 filed by Osaka Kabushiki Gaisha in 1969 provides for the depilation of skins by treatment with an aqueous solution containing 2 to 5% sodium hydroxide, 0.3 to 1.5% hydrogen peroxide (the percentage relates to the weight of the salted skins) and a pH regulating solution, e.g. potassium carbonate, in a quantity sufficient to maintain it at between 10.0 and 12.5.

In 1980, Russian patent no. 931.744 filed by SAVINA et al proposed the steepage of skins with hydrogen peroxide and a pretreatment with an aqueous solution of polyvinyl alcohol before tanning. In 1983, Brazilian patent application no. 8304115 filed by Peroxidos Do Brazil Ltda disclosed a process for the depilation of skins with peroxides in an alkaline medium (e.g. 0.5 to 8% hydrogen peroxide and 2 to 8% sodium hydroxide, based on the weight of the salted skins) and in the presence of a process control agent (e.g. stannates, sulphates, silicates, amines, amides, polyols, gluconic acid and esters thereof, used either separately or together with the solid residue obtained from the liquor formed in the process).

Finally, in 1990, an International Patent Application PCT/US89/03100 filed by AMERICAN BIOGENETICS CORPORATION disclosed a process for the solubilisation of materials consisting substantially of keratin (e.g. different types of hair) in a solution containing at least 0.1% hydrogen peroxide at ambient temperature and atmospheric pressure. The mixture thus obtained which is rich in peptides is hydrolysed in an acid medium thus giving a new mixture rich in cysteine derivatives used mainly to complete animal rations.

In a general manner, what is observed as a restriction common to the prior disclosed peroxide-based processes is the high level of intumescence of the depilated leather caused by the action of caustic alkali even in the presence of process regulating agents as provided for by Japanese patent application No. 54-10601 and Brazilian application no. 8304115 mentioned above. This is due to the large amount of water which penetrates into the skins due to osmotic forces. Part of this water usually combines with the lyophilic groups of albumen molecules by means of residual valency. Apart from this, ions present in the depilation solution, particularly the hydroxyl ions, cause the skins to puff up strongly. This phenomenon is inevitable in such processes which generally use a bath:skin ratio of the order of 100 to 150% based on the weight of the salted skins and a long operating time for this solution to have complete chemical effect on the hair and the epidermal system.

The immediate consequence of such strong intumescence of the skin is an inefficient unfolding of the fibres due to a decrease in the cohesion of the collagen (damage of the hair side) which becomes more perceptible after tanning. Depilation of the skins would take place efficiently as a result, once the phenomenon associated with this is separated from the intumescence. The depilation mechanism basically involves the absorption of the depilation solution in the capillary spaces of the skins as a result of capillary forces. In this way, a contact is established between the chemical agents and the hair as well as the epidermal system causing a chemical oxidation of these which are subsequently eliminated by mechanical action. Considering that these phenomena occur simultaneously, a serious problem is presented in seeking to dissociate depilation from intumescence in processes conducted in the presence of caustic alkali. Investigations in this respect have been carried out and an absorption of water by the skins has been determined of 30–60% by weight based on the salted skins in both cases. This absorption is high considering that, in the conventional process, sodium sulphide is used in quantities usually not exceeding 15% of the salted skin.

In view of these specific disadvantages inherent in every existing chemical process for the depilation of skins, especially when oxidising agents are used, it has been shown that up till now no convenient method exists for achieving compatibility between a high quality depilated skin and a low production of effluent as well as a reduced operating time.

It is the objective of the present invention to ameliorate or overcome one or more disadvantages as described above.

An improved process is thus proposed for the depilation of animal skins during which the skin is kept in contact with an oxidising solution until the hair is oxidised to the desired level and this is followed by a mechanical stage for appropriatly removing the hair, which is characterised by the use of the above-mentioned oxidising solution in the form of foam.

One of the main advantages of the process for the depilation of skins according to the present invention is that it enables the operator to select a low operating temperature and to control the depilation reaction with the aim of significantly reducing the intumescence in many cases. Another advantage of the process is to allow, in many cases, a considerable reduction in the operating time as a result of improved depilation efficiency. The direct consequence of this fact is the possibility of increasing the productivity of skin depilation in conventional equipment or equipment modified for this purpose.

Another advantage of the invention process is the reduction in the quantities of effluent produced, due to the use of a low bath ratio during the process and mainly the fact that, in many cases, these effluents do not have any noxious effect on the environment. Another advantage of this process, also resulting from the low bath ratio and the use of hydrogen peroxide, for example, in an alkaline medium or of peracetic acid in an acid medium under the conditions described above, is the additional bleaching effect which provides a better quality of the depilated skins.

According to a preferred embodiment of the present invention, the depilation process makes it possible to use a combination of:

a) an oxidising solution in the form of foam which permits a complete homogenisation of the chemical agents with the hair and the epidermal system b) a low bath ratio during the oxidative step which minimises the water absorption by the skins, which is the main cause of intumescence c) a high concentration of chemical agents in the depilation solution, which can be considered as the main factor for increasing the rate of oxidation of the hair and the removal of the epidermal system.

The process described by the present invention can be carried out in any conventional chamber or chamber modified for carrying out the depilation of animal skins, preferably cylinder beater mills, mulinet-type mills or similar, and consists basically of the treatment of these skins with an oxidising solution usually containing from 0.5 to 5.0% oxidising agent, from 0.5 to 5% of a pH regulator and from 0.3 to 2.0% of a surfactant composition, followed by a mechanical stage. All the percentages are the weight of active ingredient based on the weight of the salted skins.

As oxidising agent, chlorinated compounds can be used, particularly chlorine dioxide or sodium hypochlorite, but preferably peroxide compounds and particularly hydrogen peroxide and peracetic acid are employed. These compounds can be used as such or prepared in situ in accordance with the compound selected and known operating practices. The pH regulating agents include, especially when the depilation is carried out in an alkaline medium, alkalis and/or alkali metal or alkaline earth carbonates used as such or prepared in situ but particularly sodium hydroxide, ammonium hydroxide and sodium carbonate. In the case of depilation in an acid medium, inorganic or organic acids can be used as such or prepared in situ but particularly sulphuric acid and formic acid.

As surfactant compound, either non-ionic or ionic, such as anionic, surfactants can be employed. The surfactants can be used as supplied or prepared in situ in accordance with operating practice.

The nonionic compounds can conveniently be selected from amine oxides or ethoxylates. The amine oxides often contain at least one alkyl substituent of at least C9 to C18 in length, and in many instances containing a C12 to C14 alkyl substituent. The remaining alkyl groups are usually either methyl or ethyl, as for example in a C12–C14 alkyl dimethyl amine oxide. The ethoxylates can be an aliphatic or alkylphenol ethoxylate, the hydrophobic moiety usually comprising from 9 to 20 carbons and the hydrophilic ethoxylate moiety usually containing from 7 to 15 ethylene oxide units. Desirable ethoxylates include nonylphenol ethoxylates containing at least 9 ethylene oxide units.

The anionic surfactants can be based on carboxylate or sulphonate groups, i.e. be either soaps or synthetic surfactants. The soaps can be derived from naturally occuring plant or animal products such as coconut oil and related oils, oleic acid and/or olein. The synthetic surfactants can suitably comprise alkylaryl sulphonates, such as an alkyl benzene sulphonate, and preferably one in which the alkyl group contains from 10 to 14 carbons, as in dodecylbenzene sulphonate.

These compounds can be used as received or formulated in situ in accordance with operating practice. The preparation of foamed oxidising solution can take place outside the chamber in which the depilation is carried out or directly in this chamber. Preferably, it is recommended to generate the oxidising foam externally, either using conventional foam making equipment or by adapting the existing apparatus employed for a depilation process, desirably using the injection of air into the above-mentioned solution or less preferably using spray jets. It is desirable to generate a consistent foam which is subsequently injected continuously into the chamber containing the salted skins. The oxidant may be present at the time of foam generation or may be introduced into an already formed foam.

The bath ratio to be used during the oxidation stage is controlled, preferably not exceeding 50% by weight and often at least 15% by weight. The term "bath ratio" is understood to mean 100 times the quotient of the weight of the solution contacting the skins ($W_{Sol}$) by the weight of the salted skins determined at the beginning of steepage ($W_{Skin}$). In the oxidation stage, the solution comprises either the weight of the oxidising solution before it is foamed or the total weight of the foam solution plus subsequently added oxidant solution, as the case may be.

If depilation is carried out in the alkaline medium using hydrogen peroxide, for example, the pH is usually adjusted to 9.0–12.5 by means of the pH regulators mentioned above. If desired, as well as pH regulators, it is possible to incorporate one or more stabilisers for hydrogen peroxide, the selection taking into account the existing pH and suitability of the stabiliser for chelating the anticipated impurities. If depilation is carried out in the acid medium using peracetic acid, for example, the pH is usually adjusted to 2.0–3.5 in the same way as above. The process temperature is between 15° and 35° C., but particularly between 20° and 30° C. and the oxidation time is between 2 and 4 hours but particularly 2 hours, the chamber operating continuously at a rate of 5 to 10 rpm. Under such conditions, an improved homogenisation of the depilation solution in the form of foam takes place with the hair and the epidermal system, thus facilitating the chemical oxidation and at the same time avoiding large amounts of liquid being absorbed by the skin.

When the hairs have been appropriately oxidised, the foam is preferably caused to collapse by the addition of 0.01 to 0.1% by weight of an anti-foaming agent, preferably a silicone emulsion. Subsequent to the steeping or defoaming step, the liquid effluent is drained and the skins are preably washed by the addition, conveniently of from 15 to 50% by weight water. In the case of the oxidative stage being carried out in an acid medium, it is more appropriate to introduce 0.5 to 2.0% of a pH regulator, preferably sodium or calcium hydroxide and sodium carbonate into the wash water. During the washing/mechanical stage, it is often convenient to employ a bath ratio of between 15 and 50% by weight, and in many instances between 25 and 35% by weight.

The chamber is desirably kept in motion continuously at a rate of 5 to 10 rpm for a further 2 to 4 hours for the oxidised hair to be removed by the mechanical action and the skins are bleached by the action of the residual oxidising agent. This washing stage with water in the presence or absence of a pH regulator can result in an improvement in the depilation of the skins due to mechanical action.

If improved bleaching is desired, it can be achieved by adding additional oxidising agent, particularly hydrogen peroxide. Another possibility, if desired, is to use the effluent formed in this stage and consisting mainly of peptides as a starting product for process described in the International Patent application PCT/US89/03100 described above.

Having described the invention hereinbefore in general terms, specific embodiments thereof are hereinafter described more fully by way of example only, without these limiting the scope of the subject matter claimed.

In all the Examples, the percentages referred to are based on the weight of the salted skin.

EXAMPLE 1

2 kg of salted cow hide were subjected to the following operations in a PVC cylinder beater mill:

1. Washing with 120% water, at 25° C., with continuous agitation at 10 rpm over 30 minutes.
2. Drainage of the liquid.
3. Steepage in 120% water in the presence of 0.15% humectant surfactant (nonylphenolethoxylate, e.g. Renex 95) at 25° C. with continuous agitation at 10 rpm over 6 hours.
4. Drainage of the liquid.
5. Formation of foam from an oxidising solution at 25° C. consisting of:
   50.0% water
   2.0% sodium hydroxide, as 100%
   1.5% hydrogen peroxide, as 100% and
   0.5% C12–C14 amine alkyl dimethyl oxide.
6. Maintaining the foam in contact with the skins being agitated continuously at 10 rpm for 120 minutes.
7. Causing the foam to collapse with 0.05% of an emulsion of silicone anti-foaming agent (e.g. Wacker SE 39).
8. Drainage of the liquid effluent formed.
9. Addition of 35% by weight of water at 25° C., to the cylinder beater mill which is continuously agitated at 10 rpm. Usually 120 minutes are sufficient for depilation to be completed.
10. Drainage of the liquid effluent formed.
11. Discharge of the skins which are then subjected to subsequent treatment and operations for tanning purposes.
12. Assessment: At the end of stage 11, the skins are depilated, bleached and have a low degree of intumescence (7% by weight absorption of water based on the weight of the salted skins).

EXAMPLE 2

The procedure of Example 1 was repeated on another 2 kg salted cow hide in a PVC cylinder beater mill, except that in stage 5, the foam was generated at 25° C. from an oxidising solution consisting of:

15.0% water
2.0% sodium hydroxide, as 100%
1.5% hydrogen peroxide, as 100% and
0.5% C12–C14 alkyl dimethylamine oxide at 25° C.

Assessment: At the end of stage 11, the skins were depilated, bleached and had a low degree of intumescence (3% by weight absorption of water based on the weight of the salted skins).

EXAMPLE 3

The procedure of Example 1 was repeated on another 2 kg salted cow hide in a PVC cylinder beater mill, except that in stage 5, the foam was generated at 25° C. from an oxidising solution consisting of:

15.0% water
2.0% sodium hydroxide, as 100%
1.5% hydrogen peroxide, as 100% and
0.5% nonylphenol ethoxylates with 9 moles ethylene oxide Assessment: At the end of stage 11, the skins were depilated, bleached and had a low degree of intumescence (3% by weight absorption of water based on the weight of the salted skins).

EXAMPLE 4

The procedure of Example 1 was repeated on another 2 kg salted cow hide in a PVC cylinder beater mill, except that in stage 5, the foam was generated at 25° C. from an oxidising solution consisting of:

15.0% water
2.0% sodium hydroxide, as 100%
1.5% sodium carbonate, as 100%
1.5% hydrogen peroxide, as 100% and
0.5% C12–C14 alkyl dimethylamine oxide Assessment: At the end of stage 11, the skins were depilated, bleached and had a low degree of intumescence (3% by weight absorption of water based on the weight of the salted skins).

EXAMPLE 5

The procedure of Example 1 was repeated on another 2 kg salted cow hide in a PVC cylinder beater mill, except that in stage 5, the foam was generated at 25° C. from an oxidising solution consisting of:

50.0% water
0.2% hydrogen peroxide, as 100%
1.5% peracetic acid, as 100%
1.5% dodecylbenzene sulphonic acid, as 100%6.

Assessment: At the end of stage 11, the skins were depilated, bleached and had a low degree of intumescence (5% by weight absorption of water based on the weight of the salted skins).

EXAMPLE 6

The procedure of Example 1 was repeated on another 2 kg salted cow hide in a PVC cylinder beater mill, except that in stage 5, the foam was generated at 25° C. from an oxidising solution consisting of:

50% water
2.0% sodium hydroxide, as 100%
1.5% hydrogen peroxide, as 100% and
0.75% liquid coconut oil soap, as 30%.

Assessment: At the end of stage 11, the skins were depilated, bleached and had a low degree of intumescence (5% by weight absorption of water based on the weight of the salted skins).

EXAMPLE 7

The procedure of Example 1 was repeated on another 2 kg salted cow hide in a PVC cylinder beater mill, except that in stage 5, the foam was generated at 25° C. from an oxidising solution consisting of:

50% water
2.0% sodium hydroxide, as 100%
0.75% oleic acid, as av 90/100% and
1.0% liquid coconut oil soap, as 30%.

In a second difference, in stage 6, the skins were maintained in contact with the peroxide-free foam for 15 minutes. Then, 1.5% by weight of hydrogen peroxide, as 100%, was introduced into the foam and the resultant oxidising foam was maintained in contact for a further 105 minutes.

Assessment: At the end of stage 11, the skins were depilated, bleached and had a low degree of intumescence (5% by weight absorption of water based on the weight of the salted skins).

We claim:

1. In a process for the depilation of animal skins in which the skin is maintained in contact with an oxidising solution until the hair is oxidised to the desired level and this is followed by a mechanical stage for the removal of the hair, the improvement wherein the oxidising solution is employed in the form of foam, said foam containing 0.5 to 5.0% by weight of a peroxide compound based on the salted weight of the skins.

2. A process according to claim 1 wherein said foam is produced from an oxidising solution containing said peroxide compound.

3. Process according to claim 1 characterised in that the peroxide compound is hydrogen peroxide or peracetic acid.

4. Process according to claim 1 characterised in that the foam is produced within a chamber in which depilation takes place.

5. Process according to claim 1 characterised in that the oxidising solution contains from 0.5 to 3% by weight of a pH regulating agent based on the wet skin weight.

6. Process according to claim 5 characterised in that the pH regulating agent is an alkali and/or alkali metal or alkaline earth carbonate.

7. Process according to claim 5 characterised in that the pH regulator is an inorganic or organic acid.

8. Process according to claim 1 characterised in that the oxidising solution contains from 0.3 to 2.0% by weight of a surfactant composition based on the salted weight of the skins.

9. Process according to claim 1 characterised in that 0.5 to 5.0% by weight of a peroxide compound, from 0.5 to 3% by weight of a pH regulating agent and from 0.3 to 2.0% by weight of a surfactant composition are present in an oxidising solution from which foam is produced, percents being based on the wet weight of the skins.

10. Process according to claim 3 or 9 characterised in that in the oxidative stage, the bath ratio of oxidising solution to skins is from 15 to 50% by weight, thereby reducing the amount of effluent.

11. Process according to claim 3 or 9 characterised in that the oxidising foam is caused to collapse by bringing it into contact with 0.01 to 0.1% by weight of an anti-foaming agent when the hair has been oxidised to the desired level.

12. Process according to claim 11 characterised in that the anti-foaming agent comprises a silicone anti-foaming emulsion.

13. Process according to claim 3 or 9 characterised in that a process operating time of between 4 and 6 hours is employed.

14. Process according to claim 1 or 11 characterised in that a temperature of between 15° and 35° C. is employed in the foam-contact and/or water washing steps.

15. Process according to claim 1 or 9 characterised in that the oxidising foam is caused to collapse at the end of the oxidising step, the skins are separated from the residual liquor and washed with not more than 50% by weight of water, % based on the salted weight of the skins.

16. Process according to claim 1 characterized in that said foam comprises 0.5 to 5.0% by weight of a peroxide compound introduced into a preformed foam.

17. Process according to claim 1 characterised in that the foam is produced outside a chamber in which depilation takes place.

18. Process according to claim 1 wherein said agent is selected from the group consisting of sodium hydroxide, ammonium hydroxide, and sodium carbonate.

19. Process according to claim 7 wherein said acid is selected from the group consisting of sulfuric acid and formic acid.

20. Process according to claim 10 wherein said bath ratio is between 15 and 25% by weight.

21. Process according to claim 14 wherein said temperature is between 20° and 30° C.

22. Improved process for the depilation of animal skins in which the skin is maintained in contact with an oxidising solution until the hair is oxidised to the desired level and this is followed by a mechanical stage for the appropriate removal of the hair, characterised by the use of the above-mentioned oxidising solution in the form of foam, said foam containing from 0.3 to 2.0% by weight of a surfactant composition based on the salted weight of the skins, said surfactant composition containing at least one surfactant selected from the group consisting of;

a) a coconut oil soap, and/or oleic acid and/or olein, and/or b) a tertiary amine oxide, c) nonylphenol ethoxylate, and d) an alkyl benzene sulphonate.

23. Process according to claim 22 wherein said tertiary amine oxide comprises a $C_{12\text{-}14}$ amine alkyl dimethyl oxide.

24. Process according to claim 22 wherein said sulphonate comprises dodecyl benzene sulphonic acid.

* * * * *